United States Patent
Farrow

(10) Patent No.: US 7,153,294 B1
(45) Date of Patent: Dec. 26, 2006

(54) SURGICAL VACUUM CANISTER

(75) Inventor: Mark A. Farrow, Tulsa, OK (US)

(73) Assignee: H2OR, Inc., Tulsa, OK (US)

( * ) Notice: Subject to any disclaimer, the term of this patent is extended or adjusted under 35 U.S.C. 154(b) by 232 days.

(21) Appl. No.: 10/868,998

(22) Filed: Jun. 16, 2004

(51) Int. Cl.
*A61M 1/00* (2006.01)

(52) U.S. Cl. .................. 604/319; 604/317; 604/322; 604/326

(58) Field of Classification Search ......... 604/317–323
See application file for complete search history.

(56) References Cited

U.S. PATENT DOCUMENTS

| | | | |
|---|---|---|---|
| 4,275,731 A | 6/1981 | Nichols | |
| 4,275,732 A | 6/1981 | Gereg | |
| 4,301,799 A | 11/1981 | Pope, Jr. et al. | |
| D264,942 S * | 6/1982 | Schieser et al. | D9/563 |
| 4,388,922 A | 6/1983 | Telang | |
| 4,465,485 A | 8/1984 | Kashmer et al. | |
| 4,487,606 A | 12/1984 | Leviton et al. | |
| 4,507,120 A | 3/1985 | Paradis | |
| 4,681,571 A | 7/1987 | Nehring | |
| 4,870,975 A | 10/1989 | Cronk et al. | |
| 5,192,439 A * | 3/1993 | Roth et al. | 210/485 |
| 5,470,324 A | 11/1995 | Cook et al. | |
| 5,484,428 A | 1/1996 | Drainville et al. | |
| 5,620,428 A * | 4/1997 | Hand | 604/317 |
| 5,624,417 A | 4/1997 | Cook et al. | |
| 5,683,371 A | 11/1997 | Hand | |
| 5,725,516 A | 3/1998 | Cook et al. | |
| 5,792,126 A | 8/1998 | Tribastone et al. | |
| 5,960,837 A | 10/1999 | Cude | |
| 6,270,488 B1 | 8/2001 | Johnson et al. | |
| 6,656,149 B1 * | 12/2003 | Ladd | 604/73 |
| 2004/0102743 A1 * | 5/2004 | Walker | 604/319 |

* cited by examiner

*Primary Examiner*—Tatyana Zalukaeva
*Assistant Examiner*—Melanie J. Hand
(74) *Attorney, Agent, or Firm*—Fellers, Snider, Blankenship, Bailey & Tippens

(57) ABSTRACT

A vacuum canister for use in surgical or other applications. The vacuum canister of the invention includes a shell that defines an interior volume. An integral handle is provided to assist in manipulating the vacuum canister. The shell has an open top, a bottom surface and a plurality of rows of recessed structures. The plurality of rows of recessed structures defines a plurality of circumferential horizontal reinforcement ribs and a plurality of vertical reinforcement ribs therebetween. A cap is provided to seal the open top of the vacuum canister. The cap defines a vacuum orifice and a pair of instrument orifices, i.e., an ortho orifice and a patient orifice. Additionally, the cap defines a drain orifice, which is preferably of a larger size than the instrument orifices. The cap further defines a filter receptacle in communication with the vacuum orifice.

12 Claims, 5 Drawing Sheets

SURGICAL VACUUM CANISTER

BACKGROUND OF THE INVENTION

1. Field of the Invention

This invention relates generally to a vacuum canister. More particularly, the invention relates to a vacuum canister for surgical fluid collection having a large volume and having structural reinforcement members to withstand an application of vacuum to an interior of the canister.

2. Background of the Invention

Currently, vacuum canisters are used to collect and transport fluids that are produced in surgeries and other medical procedures. Vacuum canisters with portals have been used to collect fluids from collection devices by applying a vacuum to one of the portals. Previously, open topped containers were used to collect fluids by gravity flow.

A disadvantage associated with the use of open top containers includes the possibility of spillage and inadvertent contact with contaminated fluids, particularly during transport. Further, open topped containers are not suitable for the collection of fluids by vacuum.

The use of vacuum canisters has previously been impractical because large containers are susceptible to collapse when subjected to vacuum. Smaller containers are not desirable, because they fill quickly and may pose as a distraction to operating room personnel. Smaller canister, e.g., canisters of between 800 and 3,000 cubic centimeters capacity, are particularly unsuitable for surgical procedures that involve large quantities of irrigation fluids, such as arthroscopic and other types surgery. Arthroscopic surgery has been known to utilize an amount of irrigation fluid significantly in excess of 3,000 cc.

A large surface area is one disadvantage associated with large volume canisters. Since pressure forces are directly proportional to surface area, significant forces act on the outside of a large canister when a vacuum or negative pressure is pulled on the inside of the canister. One way to accommodate the large forces is by providing thick walls for the canister. However, thick walled canisters have an undesirably high material cost for their manufacture and may be heavy and difficult for operating room personnel to manipulate.

One solution to the above problems has been proposed in U.S. Pat. No. 6,270,488 to Johnson, et al. for a "Large Volume Medical Fluid Vacuum Collection Canister". Johnson, et al. teaches a large volume medical fluid vacuum collection canister that includes a blow molded canister body defining a medical fluid receiving cavity. The canister body includes a pair of opposed upstanding sidewalls interconnected by a pair of opposed upstanding end walls, a top wall with an opening and an opposed bottom wall. Each sidewall includes at least one "reentrant beam portion" extending inwardly from opposed sidewall surfaces into a central region of the medical fluid receiving cavity. The "reentrant beams" from opposing sidewalls are disposed in registering alignment so that internal end faces of the beam portions abut in face-to-face relationship when the container is under vacuum to prevent collapse of the container. However, the beam portions also occupy a significant portion of the volume of the container.

Therefore, as can be seen from the above description, a vacuum canister having a relatively large volume and having the structural integrity to avoid collapsing under vacuum pressure is desired. Additionally, it is desirable for the volume of the container to be unoccupied by support members and the like, which decrease the effective volume of the container.

SUMMARY OF THE INVENTION

A vacuum canister is provided for use in surgical or other applications. The vacuum canister of the invention includes a shell that defines an interior volume. An integral handle is provided to assist in manipulating the vacuum canister. The shell has an open top, a bottom surface and a plurality of rows of recessed structures. The plurality of rows of recessed structures defines a plurality of horizontal reinforcement ribs therebetween. The plurality of rows of recessed structures also defines a plurality of vertical reinforcement ribs therebetween. Additionally, one pair of upper recessed structures defines a partial horizontal reinforcement rib and a vertical reinforcement rib extension, which provide additional support to an upper region of the canister.

A first lower concave structure and a second lower concave structure communicate with the bottom surface of the canister. The concave structures provide support and assist in removing the canister from a mold during manufacture.

A cap is provided to seal the open top of the vacuum canister. The cap defines a vacuum orifice and a pair of instrument orifices, e.g., an ortho orifice and a patient orifice. Additionally, the cap defines a drain orifice, which is preferably of a larger size than the instrument orifices. The cap further defines a filter receptacle in communication with the vacuum orifice.

DETAILED DESCRIPTION OF THE PREFERRED EMBODIMENT

Figure 6:
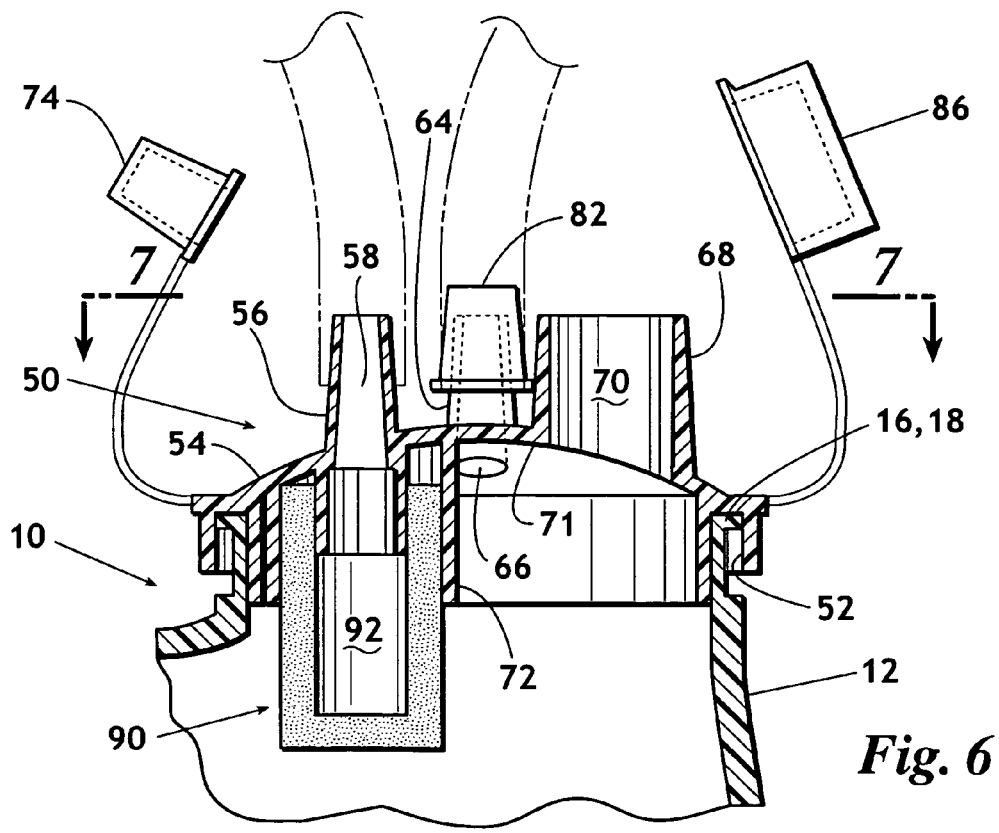
FIG. 6 is a partial cross-sectional view of the cap assembly of FIG. 4 shown affixed to the vacuum canister of FIG. 1.
Figure 8:
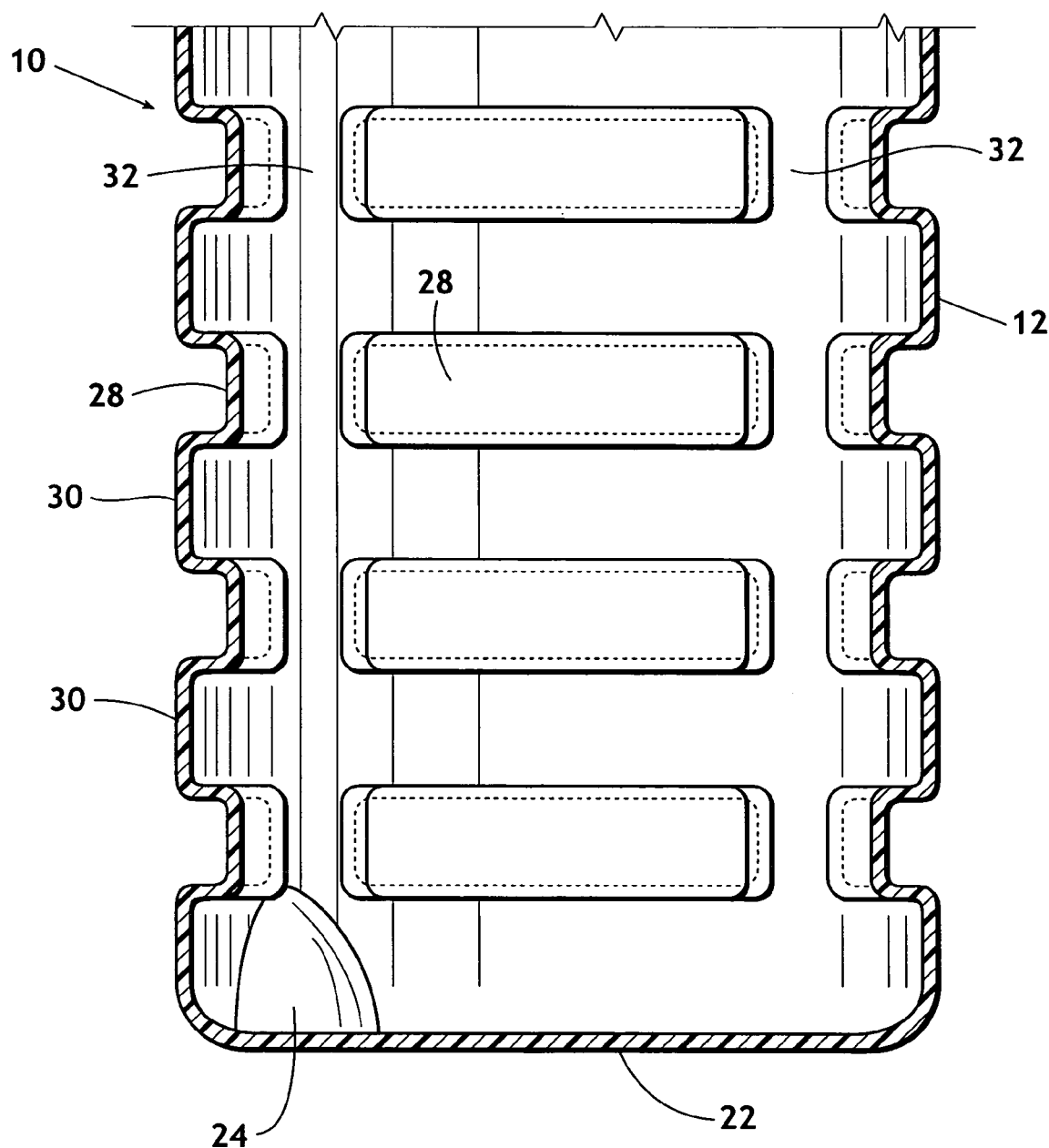
FIG. 8 is a cross-sectional view of a portion of the vacuum canister of FIG. 1.

Referring now to FIGS. 1–8, vacuum canister 10 of the invention is shown. Vacuum canister 10 includes an injection molded shell 12 that defines an interior volume 14. Shell 12 has a circular top 16 that defines a lip 18 (FIG. 6). Shell 12 is provided with an integral handle 20 and defines a bottom surface 22. A first lower concave structure 24 communicates with bottom surface 22. A second lower concave structure 26 also communicates with bottom surface 22.

Figure 1:
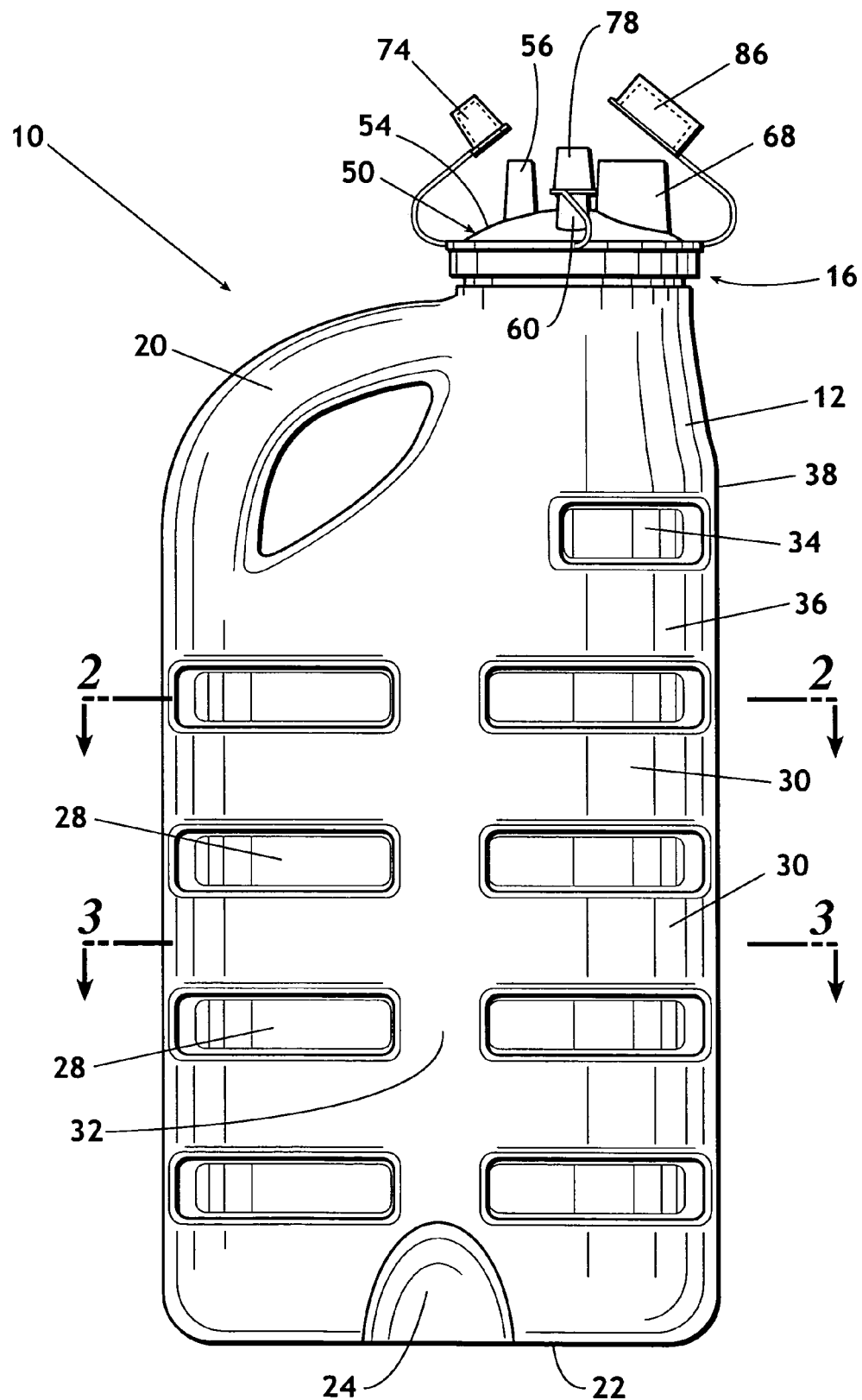
FIG. 1 is a side view of the vacuum canister of the invention.
Figure 2:
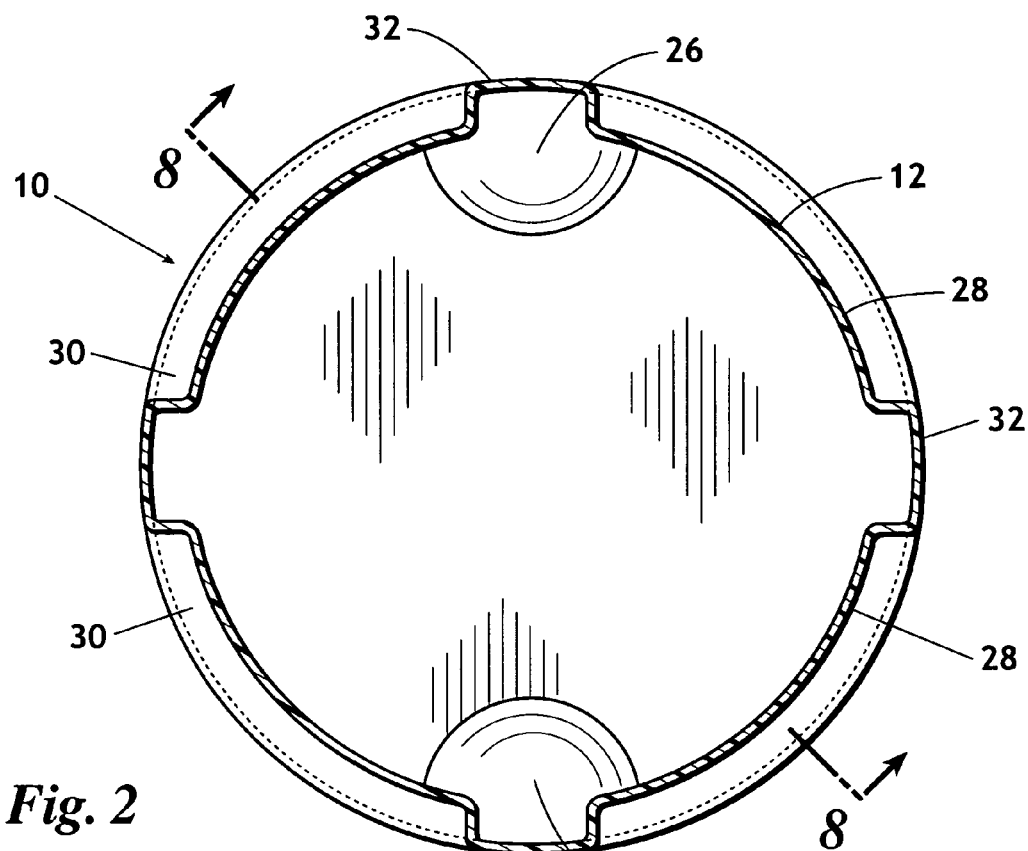
FIG. 2 is a cross-sectional view of the vacuum canister of FIG. 1 taken along lines 2—2 of FIG. 1.
Figure 3:
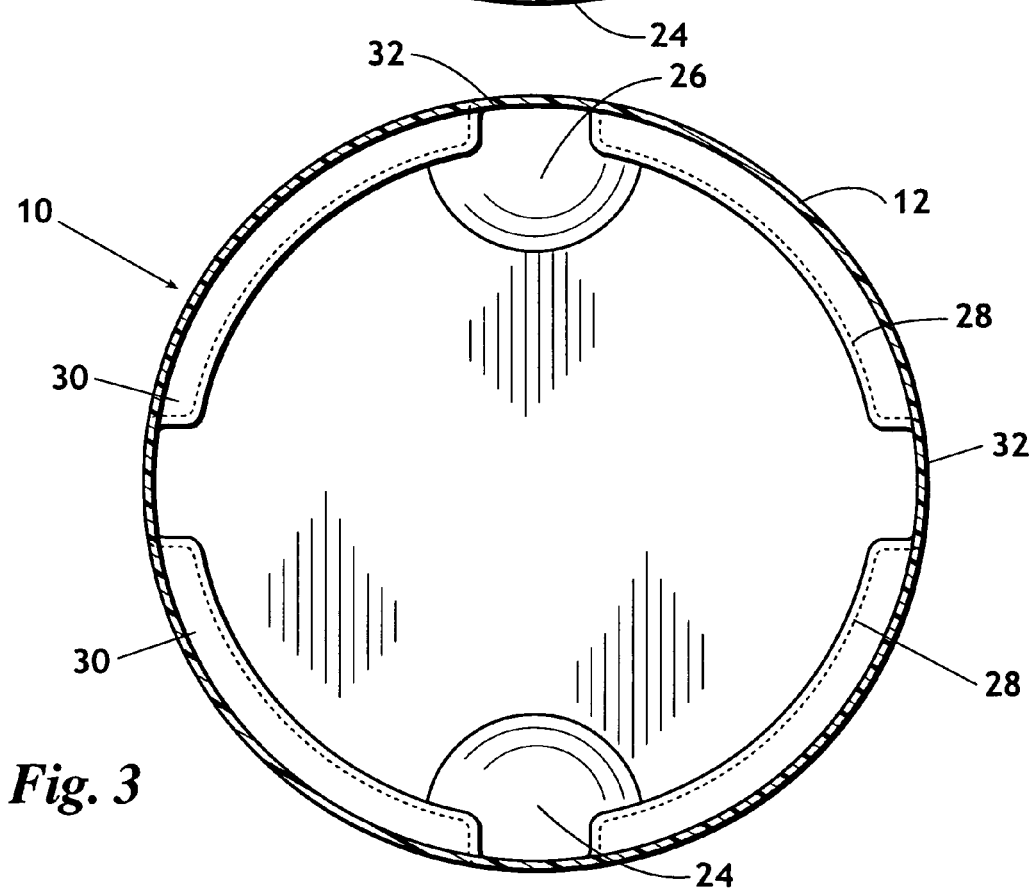
FIG. 3 is a cross-sectional view of the vacuum canister of FIG. 1 taken along lines 3—3 of FIG. 1.
Figures 4, 5:
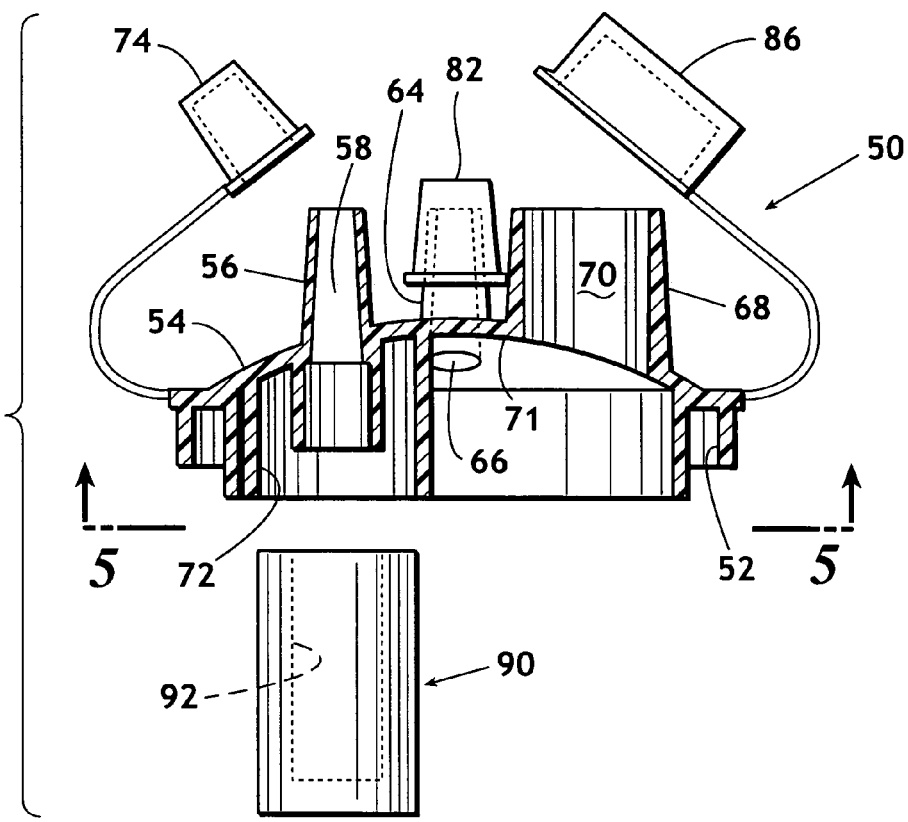
FIG. 4 is a partial cross-sectional view of a cap assembly for locating on an opening of the vacuum canister of FIG. 1.
FIG. 5 is a bottom view of the cap of FIG. 4 taken along lines 5—5 of FIG. 4.
Figure 7:
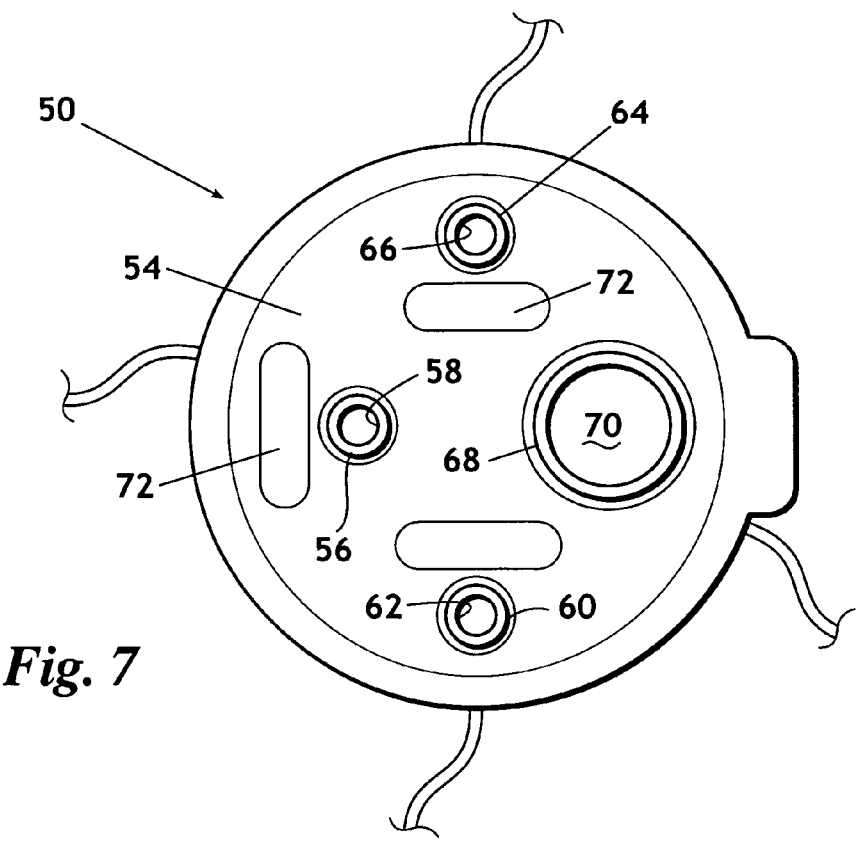
FIG. 7 is a top view of the cap assembly of FIG. 4.

Shell 12 defines a plurality of rows of recessed structures 28. Recessed structures 28 define a plurality of circumferential horizontal reinforcement ribs 30 therebetween. Additionally, a plurality of rows of recessed structures 28 defines a plurality of vertical reinforcement ribs 32 therebetween. As shown in FIG. 1, a pair of upper recessed structures 34 defines a partial horizontal reinforcement rib 36 and also defines a vertical reinforcement rib extension 38.

A cap 50 defines a circumferential snap recess 52 (FIGS. 4 and 6) for receiving lip 18 of circular top 16 of shell 12. Cap 50 has an upper surface 54 that defines a vacuum orifice riser 56 which defines a vacuum orifice 58. Upper surface 54 of cap 50 additionally defines a patient orifice riser 60, which defines a patient orifice 62. Upper surface 54 of cap 50 also defines an ortho orifice riser 64, which defines an ortho orifice 66. Additionally, upper surface 54 of cap 50 defines a drain orifice riser 68, which defines a drain orifice 70.

Cap 50 further defines a lower surface 71 that defines a filter receptacle 72. Filter receptacle 72 communicates with vacuum orifice 58. Upper surface 54 of cap 50 further defines a plurality of label surfaces 72 for facilitating the labeling of risers 56, 60, 64, and 68.

In the preferred embodiment, cap 50 is provided with vacuum orifice cap 74 that is affixed to cap 50 via a tether. Vacuum orifice cap 74 is provided for removably affixing to the vacuum orifice riser 56. A patient orifice cap 78 is affixed to cap 50 via a tether. Patient orifice cap 78 is provided for a removably affixing to the patient orifice riser 60. An ortho orifice cap 82 is additionally preferably connected to cap 50 with a tether. Ortho orifice cap 82 is provided for removably affixing to ortho orifice riser 64. Further, cap 50 is preferably provided with a drain orifice cap 86 affixed to cap 50 by a tether. The drain orifice cap 86 is provided for removably affixing to the drain orifice riser 68.

A filter member 90 is preferably provided for locating within filter receptacle 72 defined on lower surface 71 of cap 50. Preferably filter member 90 is constructed of porous plastic and defines an internal chamber 92. However, other suitable materials may also be used.

In one example of a typical use for surgical vacuum canister 10, a vacuum pump or other device is connected via tubing to vacuum orifice riser 56. Pressure within interior volume 14 of surgical vacuum canister 10 is then lowered, which creates a partial vacuum within interior volume 14. Filter member 90 assists in preventing fluids or other materials from being sucked through vacuum orifice riser 56.

In a surgical environment, a vacuum pump may be used to lower the pressure within interior volume 14 to a pressure less than ambient conditions, e.g., to 1 psi or less. Tubing may be connected to patient orifice riser 60, which may be connected to a surgical instrument for removing fluids from a patient's body cavity and depositing them into vacuum canister 10 or for other purposes. Additionally, tubing may be connected to orifice riser 64 for connecting to an additional device, such as a floor aspirating tube for removing fluids from a floor of an operating room and transferring the fluids into vacuum canister 10. During operation, cap 86 preferably remains closed to prevent air from entering into vacuum canister 10, which would be detrimental to the performance of attached vacuum devices.

A preferred size of vacuum canister 10 is 13,000 ml. The relatively large size of vacuum canister 10 functions to save surgical time by eliminating frequent canister changes when fluid is abundant. Integrated handle 20 makes transporting a full vacuum canister 10 simple and efficient.

A problem associated with vacuum canisters in general is the tendency of the canister to collapse under the force of the applied vacuum. This problem is exacerbated in large canisters, such as a canister of 13,000 ml. Regardless of the size of the container, circumferential horizontal ribs 30, or hoops, provide strength to enable the vacuum canister to resist bowing or partial collapse of the sidewalls, as well as preventing canister failure or total collapse. Additionally, vertical reinforcement ribs 32, or longitudinal ribs, function to reinforce the canister and prevent the canister from collapsing in an accordion-like fashion. The combination of horizontal and vertical reinforcement ribs 30 and 32 provide a very strong shell 12 of canister 10, which permits the use of lightweight materials and thin walled construction.

A preferred material for shell 12 is polypropylene #5 having a wall thickness of 3/16". Lightweight materials and thin walled construction are beneficial for reducing the weight of canister 10, which is important because a full canister can be heavy and difficult for some operating personnel to move.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A vacuum canister comprising: a shell defining an interior volume, said shell having an open top, a bottom surface and a plurality of rows of recessed structures; the plurality of rows of recessed structures defining a plurality of circumferential horizontal reinforcement ribs therebetween, said horizontal reinforcement ribs being configured to resist applied vacuum to maintain substantially constant said interior volume; the plurality of rows of recessed structures defining a plurality of vertical reinforcement ribs therebetween, said vertical reinforcement ribs being configured to resist applied vacuum to maintain substantially constant said interior volume; and a cap defining a vacuum orifice and an instrument orifice.

2. The vacuum canister according to claim 1 further comprising:
a handle integral with said shell.

3. The vacuum canister according to claim 1 further comprising: a first lower concave structure in communication with said bottom surface; and a second lower concave structure in communication with said bottom surface; said first and said second lower concave structures being configured to reinforce said shell to resist applied vacuum and to maintain substantially constant said interior volume.

4. The vacuum canister according to claim 1 wherein the vacuum canister further comprises:
a pair of upper recessed structures defining a partial horizontal reinforcement rib.

5. The vacuum canister according to claim 1 wherein the vacuum canister further comprises: a vertical reinforcement rib extension, said vertical reinforcement rib extension being configured to resist applied vacuum to maintain substantially constant said interior volume.

6. The vacuum canister according to claim 1 wherein:
said vacuum orifice is defined by a vacuum orifice riser for receiving a vacuum line.

7. The vacuum canister according to claim 1 wherein:
said instrument orifice is defined by an instrument orifice riser for receiving an instrument line.

8. The vacuum canister according to claim 1 wherein the cap:
further defines a third orifice.

9. The vacuum canister according to claim 8 wherein:
a third riser defines said third orifice.

10. The vacuum canister according to claim 1 wherein: said cap further defines a drain orifice.

11. The vacuum canister according to claim 1 wherein: said cap further defines a filter receptacle in communication with said vacuum orifice.

12. The vacuum canister according to claim 1 wherein: an upper surface of said cap further defines a plurality of label surfaces for labeling the orifices.

* * * * *